United States Patent
Martin et al.

(12)

(10) Patent No.: US 6,203,784 B1
(45) Date of Patent: *Mar. 20, 2001

(54) DEPILATORY COMPOSITIONS WITH THIXOTROPIC AGENTS

(75) Inventors: Georges Martin, Saint Benoit; Philippe Ledon, Le Coudray; Hubert Delagneau, Mainvilliers, all of (FR)

(73) Assignee: Reckitt Benckiser France, Massy Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/730,305

(22) Filed: Oct. 11, 1996

(30) Foreign Application Priority Data

Oct. 16, 1995 (GB) .................................................. 9521101

(51) Int. Cl.⁷ ........................................................ A61K 7/15
(52) U.S. Cl. ........................... 424/73; 424/400; 424/401; 514/557
(58) Field of Search ............................ 424/73, 400, 401; 574/557

(56) References Cited

U.S. PATENT DOCUMENTS

| | | | |
|---|---|---|---|
| 3,271,258 | 9/1966 | Zviak et al. | 167/89 |
| 4,111,653 | 9/1978 | Lindemann et al. | 8/161 |
| 4,618,344 | 10/1986 | Wells | 8/161 |
| 5,653,970 | * 8/1997 | Vermeer | 424/70.24 |

FOREIGN PATENT DOCUMENTS

| | | |
|---|---|---|
| 0 307 129 A1 | 3/1989 | (EP) . |
| 0 532 219 A2 | 3/1993 | (EP) . |
| 1463966 | 2/1977 | (GB) . |
| 2 152 525 | 8/1985 | (GB) . |
| WO 93/08791 | 5/1993 | (WO) . |

OTHER PUBLICATIONS

WPI Abst. 92–255639/31 and JP 040173725.

WPI Abst. 85–168487/28 and JP 6000097912A.

Copy of GB Search Report dated Jan. 31, 1996 for GB 9521101.7.

Copy of PCT Search Report dated Jan. 23, 1997 for PCT/GB96/02497.

* cited by examiner

*Primary Examiner*—Neil S. Levy
(74) *Attorney, Agent, or Firm*—Fish & Richardson P.C.

(57) ABSTRACT

A depilatory composition has improved rinsing properties by the inclusion of from 0.25% to 6% of a thixotropic agent and from 5% to 10.5% of fatty materials. Preferred thixotropic agents are smectite clays, bentonites and synthetic nectorite clays.

3 Claims, No Drawings

DEPILATORY COMPOSITIONS WITH THIXOTROPIC AGENTS

BACKGROUND OF THE INVENTION

The present invention relates to compositions for the treatment of hair and, in particular, to hair treatment compositions having improved rinsing properties. The invention relates especially to depilatory compositions, but will also find application in perming compositions.

Depilatory compositions are conventionally applied to the skin in the form of a cream, lotion, gel or mousse. After a period of time, the depilatory composition is removed by suitable means, such as by the use of a spatula. The active depilatory ingredient of the composition is conventionally an alkali metal salt or alkaline earth metal salt of an alpha or beta mercapto-carboxylic acid, such as potassium or calcium thioglycolate. These materials act by penetrating the hair and destroying the cystine bonds between the hair molecules. This weakens the hair to such an extent that the action of scraping and wiping away the depilatory composition causes the hair to break off at skin level, so that the hair may be removed.

A particular problem with compositions of this type is that the composition is difficult to remove completely from the skin and cannot be removed easily by simply rinsing away the composition. A heavy or vigorous mechanical scrubbing or scraping action is required, for example with a spatula, which can be a cause of considerable discomfort and inconvenience. Accordingly, the present invention seeks to provide hair treatment compositions, in particular depilatory compositions, having improved rinsing properties.

For conventional depilatory compositions in the form of a cream, lotion, gel or mousse, the emulsion is normally stabilized by including a relatively high amount of thickener in the composition. For example, conventional thickeners, which will be well known to those skilled in the art, are generally present at levels of up to 30% w/w. Alternatively, depilatory creams, lotions and gels can be formulated to give a stable emulsion by including high levels of fatty materials in the depilatory composition. In such compositions, either no thickener is present, or a small amount of thickener may be present.

In both cases, however, good rinsability of the depilatory composition from the skin will not be achieved. In the case where a high level of thickener is present, there will be such strong steric interactions between the polymeric materials in the emulsion that it is not possible to remove the depilatory composition quickly and easily from the skin by the mechanical action of water together with a light rubbing action. Where high levels of fatty materials are present, the texture or "body" of the depilatory composition will be too strong to allow the composition to be rinsed simply from the skin.

For example, International Patent Publication Ser. No. WO 93/08791 (The Boots Company PLC) describes depilatory formulations including, inter alia, smectite or kaolin clays such as bentonite. The clays are said to improve the feel of the depilatory composition on the skin and to reduce the unpleasant smell associated with the depilatory agent. However, the compositions described in WO 93/08791 would not have the improved rinsability of the depilatory compositions of the present invention. That is, the compositions described in WO 93/08791, containing the levels of thickeners and fatty materials as specified, would not be able to be rinsed simply from the skin by the mechanical action of water together with a light rubbing action.

However, in accordance with the present invention, we have found that it is possible to formulate a depilatory composition which is sufficiently stable to provide a good depilatory product, but which has weak enough steric interactions between the polymeric materials in the composition to provide improved rinsing properties.

SUMMARY OF THE INVENTION

It has now been found surprisingly that the incorporation in a hair treatment composition of a viscosity enhancer which imparts a shear sensitive structure to the composition (hereinafter called a thixotropic agent) provides such improved rinsing properties. The incorporation of a thixotropic agent in a depilatory composition allows the composition to be rinsed off the skin simply, for example, by the mechanical action of water from a shower together with a light rubbing action. The need for heavy scrubbing or scraping with a spatula or the like is thus avoided. The sensitivity of the composition to shear forces can be made so acute that the mere mechanical action on the skin of water from the shower is sufficient for effective removal of the composition, but such a degree of shear sensitivity may adversely affect other properties of the composition.

Accordingly, the first aspect of the present invention provides a depilatory composition including a functional amount of a thixotropic agent, which composition has a shear sensitive structure.

By this we mean that the sensitivity of the depilatory composition of the present invention to shear forces is such that the mechanical action on the skin of water alone, or the mechanical action on the skin of water together with a light rubbing action, is sufficient to remove the composition from the skin.

In accordance with a second aspect of the present invention there is provided the use, in a depilatory composition, of a functional amount of a thixotropic agent effective to impart a shear sensitive structure to the composition.

DETAILED DISCLOSURE

The compositions of the invention may include any suitable mineral or organic thixotropic agent, but particularly preferred thixotropic agents include smectite clays, synthetic hectorite clays such as Laponite LS from Laporte, colloidal montmorillonites such as those available under the trade name Gelwhite from Southern Clay Products Inc, USA and Laporte, silicoaluminate clays such as the collidal magnesium aluminium silicate derived from natural smectic clay obtainable as Veegum from Vanderbilt Products (USA) and xanthan gums such as Keltrol T from Kelco.

The thixotropic agent is preferably present in an amount of 0.25% to 6% w/w, most preferably 0.25% to 2% w/w, and especially 0.25% to 1% w/w.

The compositions of the invention preferably include 1.5% to 8% w/w (most preferably 2.5% to 5% w/w) of an active depilatory agent. In the compositions of the invention, the depilatory agent will preferably act by reducing disulfide bonds in the hair and in principle any suitable reducing agent may be used. Suitable examples include mercaptans and sulfides such as organic sulfides, especially alkyl sulfides. Preferred depilatory agents are alkaline salts of thioglycolic acid such as the lithium, sodium, potassium or calcium salts. The potassium and calcium salts, alone or in mixture, are particularly preferred. Other suitable depilatory agents include thioglycerol, mercapto propionic acid and dithioerythritol.

Optionally, the compositions of the invention may further include an accelerator to facilitate the action of the depilatory agent, preferably in an amount of 3% to 10% w/w and particularly preferably not less than 5% w/w. A preferred accelerator is urea.

Additional polymeric thickening agents may be included in the compositions of the invention in amounts of 0 to 2% w/w, preferably 0 to 0.5% w/w, especially 0.1% w/w. Appropriate thickening agents can also contribute to the stability of the composition.

The compositions of the invention will preferably have a pH of at least 10.5, particularly preferably 11.5 to 12.7 (whilst the pH could be higher than 12.7, the latter value is the highest permitted in Europe). Suitable materials for achieving the desired pH include calcium hydroxide (at a concentration of 2% to 4% w/w) or alkaline silicates such as meta- or trisilicates.

The compositions of the invention will also desirably include texturizing agents to provide the composition with a desired texture or "body" whereby the depilatory composition can be maintained on the skin in contact with the hair and in the correct quantity to achieve a satisfactory degree of hair digestion in a suitable time. Suitable materials for this purpose are generally known in the art and include, for example, fatty materials such as fatty alcohols (for example cetostearyl alcohol) alone or in combination with paraffin oils. These materials may be present in amounts of, for example, 5% to 20% w/w, preferably 8% to 15% w/w. An appropriate emulsifier such as a non-ionic ethoxylated fatty alcohol may also be included, suitably in an amount of 1% to 5% w/w. An example of a suitable emulsifier is Ceteareth 20, supplied by Henkel. The compositions of the invention may further include buffering agents (such as calcium hydroxide) (2% to 6% w/w ), cosmetic ingredients such as moisturizing agents (for example Aloe Vera extracts) and skin smoothing agents (for example, almond oil, shea butter, lanolin and allantoin), coloring agents (0.4% to 0.6% w/w) and perfumes (0.55% to 0.7% w/w), with the balance being water.

Most preferably, the amount of thixotropic agent and the amount of fatty materials present in the compositions of the invention will be adjusted to provide the best rinsing properties.

According to a further aspect of the present invention there is provided a depilatory composition having a shear sensitive structure, which composition contains 0.25% to 6% w/w of a thixotropic agent and 5% to 15% w/w fatty materials. Most preferably, the composition contains 0.25% to 2% w/w (especially 0.25% to 1% w/w) of a thixotropic agent and 8% to 10.5% w/w fatty materials.

By "fatty materials" we mean any materials commonly found in the oil phase of a cosmetic emulsion, especially materials having a hydrocarbon chain of at least six carbons of very poor water solubility, for example paraffin oil, fatty alcohols and fatty esters, and any emulsifying agents soluble in the above-mentioned materials, for example fatty alcohol ethoxylates, fatty amide ethoxylates and soaps.

EXAMPLES

The following depilatory compositions were prepared:
Composition A (Reference composition)

| | |
|---|---|
| Cetostearyl alcohol ($C_{16}$ 80%, $C_{18}$ 20%) | 8% |
| Ceteareth 20 | 2% |
| Urea | 10% |
| KOH | 2.7% |
| Thioglycolic acid | 4.5% |
| Calcium hydroxide | 2.9%* |
| Dye | 0.5% |
| Balance, water | |

*Calcium hydroxide is added in an amount to achieve the desired pH - preferably pH 12.5

Composition B
The following pre-mixes were first prepared:

| | | |
|---|---|---|
| 1. | Laponite XLG | 1% |
| | Water | 2.0% |
| 2. | Calcium Hydroxide | 2.9% |
| | Water | 15.0% |
| 3. | Cetostearyl alcohol | 8% |
| | Polyethyleneglycol fatty alcohol | 1.25% |
| | Almond oil | 0.5% |
| 4. | Urea (technical grade) | 8% |
| | Water | 10% |

These premixes may be heated as known in the art to achieve dispersion/dissolution.

The final mixture was then prepared in the following sequence:
1. Premix 1
2. Dye (0.69%)
3. Premix 2
4. Premix 3
5. Water (12.5%)
6. Premix 4
7. Perfume (0.55%)
8. 30% Potassium thioglycolate (10.0%)
9. Water to 100%

Composition C
Composition B further including
0.5% Viscose fibers, length 1 mm and
5.0% Low density polyethylene microparticles (230 μm).

Composition D
The following pre-mixes were first prepared:

| | | |
|---|---|---|
| 1. | Calcium hydroxide | 2.9% |
| | Water | 20% |
| 2. | Cetostearyl alcohol | 8% |
| | Polyeleneglycol fatty alcohol | 2.5% |
| | Almond oil | 0.5% |
| 3. | Laponite XLG | 1% |
| | Urea (technical grade) | 8% |
| | 30% Potassium thioglycolate | 10% |
| | Water | balance |

The final mixture was then prepared in the following sequence.
1. Premix 1
2. Dye (0.69%)
3. Premix 2
4. Premix 3
5. Perfume (0.55%)

Composition A was prepared by mixing at a suitable temperature, e.g. 70° C., the emulsifier, the fatty ingredients and part of the water to form a primary emulsion. After cooling to below 40° C., the remaining ingredients were added.

In the compositions of the invention, the thixotropic agent is preferably added as a gel to the primary emulsion (e.g. premixes 1, 2 and dye in composition D).

The rinsing properties of depilatory compositions A, B and C were tested in vitro using the following protocol:

17 g of the composition was applied evenly to a "Velcro" (™) strip (5 cm×20 cm) mounted on a support. The composition was then rinsed using a warm water shower with a water output of 0.16 1/s, with the shower head maintained perpendicular to the coated "Velcro" (™) strip at a distance of 5 to 10 cm. The time taken to remove the compositions from the "Velcro" (™) strip was measured. The results are indicated in Table 1.

TABLE 1

| Composition | Rinsing time (s) |
| --- | --- |
| A | 41.3 |
| B | 13.0 |
| C | 12.3 |
| D | 13.0 |

From the above it can be appreciated that the inclusion of a thixotropic agent significantly improves the rinsability of the compositions.

Comparative tests were also conducted in vivo on 22 volunteers at the applicant's premises. The tested formulations were Composition C and, as the comparative formulation, Composition A. The results of these tests are set out below.

The volunteers were asked to compare the two compositions, by giving a rating for each composition between 1 and 10 having used the preparations, with 1 indicating very poor results and 10 indicating very good results.

| Test | Rating for Composition A | Rating for Composition C |
| --- | --- | --- |
| Easy to Remove | 6.5 | 8.0 |
| Provides soft skin | 7.0 | 8.0 |
| Easy to rinse | 6.0 | 7.5 |
| No greasy skin feel | 7.0 | 8.5 |
| Texture | 7.0 | 6.0 |
| Color | 7.5 | 6.0 |

It is apparent that Composition C was perceived by the volunteers to be superior in all respects with the exception of the color (attributable to the particular fibers used) and texture (attributable to the fibers and the microparticles).

A further test on three volunteers known to be sensitive to depilatory compositions showed no difference in skin irritancy between Composition C and Composition A.

What is claimed is:

1. A depilatory composition which consists essentially of:

1% w/w of a hectorite clay;

2–9% w/w calcium hydroxide;

8% w/w cetostearyl alcohol, 1.25% w/w polyethylene glycol fatty alcohol;

8% w/w urea;

3% w/w potassium thioglycoate; and water in sufficient amount to bring the composition to 100%.

2. A depilatory composition which consists essentially of:

1% w/w of a hectorite clay;

2–9% w/w calcium hydroxide;

8% w/w cetostearyl alcohol;

1.25% w/w polyethylene glycol fatty alcohol;

8% w/w urea;

0.5% w/w viscose fibers;

5% w/w low density polyethylene microparticles;

3% W/w potassium thioglycolate; and water in sufficient mount to bring the composition to 100%.

3. A depilatory composition which consists essentially of:

1% w/w of a hectorite clay;

2.9% w/w calcium hydroxide;

8% w/w cetostearyl alcohol;

2.5% w/w polyethylene glycol fatty alcohol;

8% w/w urea;

0.5% w/w almond oil:

0.5% w/w viscose fibers;

5% w/w low density polyethylene microparticles;

3% w/w potassium thioglycolate; and water in sufficient amount to bring the composition to 100%.

* * * * *

UNITED STATES PATENT AND TRADEMARK OFFICE
CERTIFICATE OF CORRECTION

PATENT NO. : 6,203,784 B1  
DATED : March 20, 2001  
INVENTOR(S) : Georges Martin, Philippe Ledon, and Hubert Delagneau Page 1 of 1

It is certified that error appears in the above-identified patent and that said Letters Patent is hereby corrected as shown below:

<u>Column 6,</u>  
Line 12, delete "2-9%" and insert -- 2.9% --.  
Line 24, delete "2-9%" and insert -- 2.9% --.  
Line 33, delete "W/w" and insert -- w/w --.  
Line 34, delete "mount" and insert -- amount --.

Signed and Sealed this

Sixteenth Day of October, 2001

Attest:

NICHOLAS P. GODICI  
Attesting Officer    Acting Director of the United States Patent and Trademark Office